United States Patent

Arakawa et al.

[11] Patent Number: 5,942,308
[45] Date of Patent: Aug. 24, 1999

[54] EXPANDABLE FIXING TAPE

[75] Inventors: Masaaki Arakawa; Kazuhisa Maeda; Katsumi Hori; Teiji Sakashita, all of Osaka, Japan

[73] Assignee: Nitto Denko Corporation, Osaka, Japan

[21] Appl. No.: 08/674,900

[22] Filed: Jul. 3, 1996

[30] Foreign Application Priority Data

Jul. 5, 1995 [JP] Japan .................................. 7-169706
Oct. 30, 1995 [JP] Japan .................................. 7-281468

[51] Int. Cl.$^6$ ...................................................... C09J 7/02
[52] U.S. Cl. .......................... 428/130; 428/156; 428/343
[58] Field of Search ...................... 428/343, 156, 428/130

[56] References Cited

U.S. PATENT DOCUMENTS 4,522,853  6/1985  Szone et al. .............................. 428/40

FOREIGN PATENT DOCUMENTS

0191355  8/1986  European Pat. Off. .
0648483  4/1995  European Pat. Off. .
WO9002540  3/1990  WIPO .

Primary Examiner—Jenna Davis
Attorney, Agent, or Firm—Sughrue, Mion, Zinn, Macpeak & Seas, PLLC

[57] ABSTRACT

Disclosed are an expandable fixing tape comprising a base material composed of an expandable portion and a substantially non-stretchable portion, and a fixing means provided on at least one non-stretchable portion which is present at one end of the base material, wherein the expandable portion exhibits a load of not more than 5.0 kg/25 mm at 200% expanding and a permanent set of not less than 30% under the condition of 200% expanding, and the substantially non-stretchable portion has a ductility of less than twice under a load of not more than 0.5 kg/25 mm and a base material composed of an expandable portion, which is a thin layer portion having a thin thickness, at the central portion in the lengthwise direction and substantially non-stretchable portions, which are thick layer portions having a thick thickness, at both the end portions, a fixing means provided on at least one non-stretchable portion which is present at one end of the base material, wherein the expandable portion can be expanded to the length of at least three times under a load of 1.5 kg/25 mm and has a permanent set of at least 30% under the condition of 200% expanding, and the thickness of the expandable portion is not more than 90% of the thickness of the non-stretchable portion. These tapes can be easily expanded by a weak force at use and are very practical and easily usable, and are suitably used for packaging bags, boxes, etc. or for treating sanitary articles used.

14 Claims, 5 Drawing Sheets

EXPANDABLE FIXING TAPE

FIELD OF THE INVENTION

The present invention relates to an expandable fixing tape which is suitably used, for example, for packaging bags, boxes, etc., or after using, for example, sanitary articles such as a paper diaper, a sanitary napkin, etc., for treating these sanitary articles by rounding and fixing them.

BACKGROUND OF THE INVENTION

Hitherto, as a fixing tape for, for example, paper diapers, etc., various pressure-sensitive adhesive tapes which constitutes a folded Z form as disclosed, e.g., in JP-B-58-30401, JP-B-52-47769, and JP-B-1-56163. (The term "JP-B" as used herein means an "examined published Japanese patent application.)

Since these pressure-sensitive adhesive tapes are not of a type of expanding at using, there are problems that when, for example, a used diaper, etc., is treated by rounding, the rounded diaper, etc., cannot be sufficiently fixed with the conventional pressure-sensitive adhesive tape and the tape comes off owing to a short length of the tape or since the tape is not expanded by strongly pulling the tape, the pulling force is transmitted as it is to the article, whereby the end portion of the tape fixed to the article is released.

SUMMARY OF THE INVENTION

The present invention has been made for solving the problems described above and the object of the present invention is to provide an expandable (expansible) fixing tape which can be easily expanded by a weak force at use, the expanded portion being substantially reluctant to shrink, and is very practical and easily usable.

That is, according to an aspect of the present invention, there is provided an expandable fixing tape comprising:
 a base material composed of an expandable portion and a substantially non-stretchable portion, and
 a fixing means provided on at least one non-stretchable portion which is present on at least one end of the base material,
 wherein the expandable portion exhibits a load (tension) of not more than 5.0 kg/25 mm when it is subjected to 200% expanding and a permanent set of not less than 30% under the condition of 200% expanding, and
 the substantially non-stretchable portion has a ductility of less than twice under a load of not more than 0.5 kg/25 mm.

Also, according to another aspect of the present invention, there is provided an expandable fixing tape comprising:
 a base material composed of an expandable portion, which is a thin layer portion having a thin thickness, at the central portion in the lengthwise direction and substantially non-stretchable portions, which are thick layer portions having a thick thickness, at both the end portions,
 a fixing means provided on at least one non-stretchable portion which is present on at least one end of the base material,
 wherein the expandable portion can be expanded to the length of at least three times under a load of 1.5 kg/25 mm and has a permanent set of at least 30% under the condition of 200% expanding, and
 the thickness of the expandable portion is not more than 90% of the thickness of the non-stretchable portion.

The terminology "200% expanding of the expandable portion" as used herein means that the expandable portion is expanded to have the length three times the initial length of the expandable portion, and the terminology "ductility" as used herein means the ratio (times) of the length after expansion to the initial length.

DETAILED DESCRIPTION OF THE INVENTION

Then, the present invention is described in detail.

First, various embodiments of the fixing tape of the present invention are explained based on the accompaning drawings.

Figure 1:
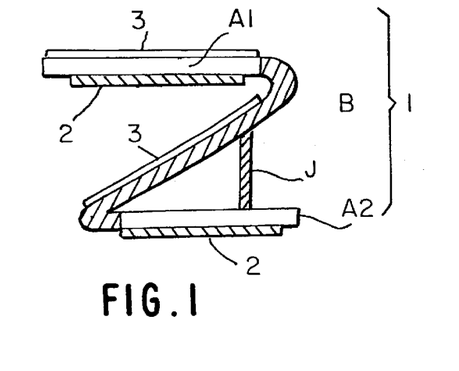
FIG. 1 is a cross sectional view showing an embodiment of the fixing tape of the present invention.

FIG. 1 is a cross sectional view showing an embodiment of the expandable fixing tape of the present invention and a base material 1, of which both the end portions are substantially non-stretchable portions A1 and A2, and the central portion is the expandable portion B, is folded two times at the expandable portion B to be constructed into a Z-form. On the inside surface of A1 and on the outside surface of the non-stretchable portion A2 is formed each of pressure-sensitive adhesive layers 2 as the fixing means, and on the outside surface of the non-stretchable portion A1 and on the surface of the expandable portion B facing the pressure-sensitive adhesive layer 2 of the inside surface of the non-stretchable portion A1 is formed each of the releasing agent layers 3. Furthermore, between the expandable portion B and the inside surface of the non-stretchable portion A2 is formed a temporary joining means J (described below) for temporarily connecting them for maintaining the Z-type form.

In the embodiment of FIG. 1, the fixing means formed on the outside surface of the non-stretchable portion A2 is necessary for fixing one end of the fixing tape to an adherend. As such a fixing means, the pressure-sensitive adhesive layer 2 as shown in FIG. 1 is preferably used, but, other fixing means such as an adhesive or a hook-form fastening object can be employed depending on the form or kind of the adherend.

Also, in the embodiment of FIG. 1, the re-peelable fixing means composed of the pressure-sensitive adhesive layer 2 is provided on the inside surface of the non-stretchable portion A1. There are some cases where such a fixing means is unnecessary according to the using mode (for example, FIG. 28). Not only the pressure-sensitive adhesive layer 2 but also other means such as an adhesive or a hook-form fastening object can be employed as the fixing means depending on the form or kind of the adherend.

Figure 2:
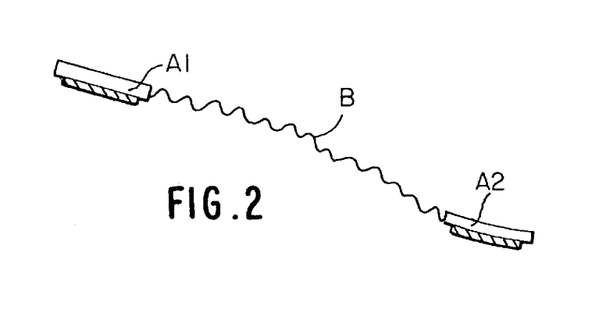
FIG. 2 is a schematic view at unfolding the fixing tape of FIG. 1.

FIG. 2 is a schematic view showing a state of unfolding and expanding the fixing tape of FIG. 1 at using the fixing tape, and for example, by pulling the non-stretchable portion A1, the temporary joining means J is released to unfold the Z-form and by further pulling the non-stretchable portion A1, the expandable portion B can be expanded to a necessary length to fix the non-stretchable portion A1 onto an adherend.

The expandable portion B is necessary for prolonging the total length of the fixing tape (at least two times) to surround an article with the tape and to fix the tape onto the article. It is preferred that the expandable portion B is expanded by a weak force at use for the purpose of reducing a stress, which is caused by pulling with a hand, by expanding of the tape, preventing one end of the fixing tape previously fixed to an article from being released, and reducing a stress caused by a little expansion of the article after rounding the article. Specifically, it is desirable that when the expandable portion is subjected to 200% expanding at 23° C., the load is not more than 5.0 kg/25 mm and particularly not more than 3.0 kg/25 mm. When the expandable property of the expandable portion B is outside the foregoing range, there are undesirable faults that a large force becomes necessary for expanding the expandable portion B to a definite length, whereby the one end portion of the fixing tape previously fixed to an article is released, and also the fixing tape is reluctant to expand and is reluctant to use.

Furthermore, for the purpose of freely controlling the total length of the fixing tape with a hand and treating (wasting) by surrounding an article having the circumference of at least three times the length of the fixing tape, it is necessary that the expandable portion B is not shrinked too much after being expanded and it is preferred that the expandable portion B does not shrink to the original length after releasing the force. Specifically, it is desirable that the permanent set (at 23° C.) at 200% expanding of the expandable portion is at least 30% and particularly at least 50%. After expanding, if the expandable portion B largely shrinks to the original state, the shrinking force is large, whereby there occurs a fault that the end portion of the fixing tape previously fixed to an article or the portion of fixing an article after rounding is released. However, the occurring of a little shrinkage is rather preferable in the point of capable of rounding an article in a strained state.

Also, since a fixing means such as a pressure-sensitive adhesive layer, an adhesive layer, a fastening object (hook-form object), etc., is formed on the substantially non-stretchable portions A1 and/or A2 for fixing an article thereto, if the expansion thereof is large, there is a possibility that the fixed portion is released by expanding, it is preferred that the non-stretchable portion is substantially reluctant to be expanded and it is desirable that the non-stretchable portions have a ductility of less than 2 times and particularly less than 1.5 times under the load of 0.5 kg/25 mm or less and at 23° C. However, the occurrence of a little expansion is preferred in the point that the concentration of stresses in the bonded portion of the expandable portion and the non-stretchable portion is absorbed by the little expansion of the non-stretchable portion, whereby the strength is retained.

Also, in the present invention, it is preferred that the thickness of the expandable portion of the central portion is thinner than the thickness near the boundary between each of both end portions of the non-stretchable portion and the expandable portion in the point that expanding starts from the central portion, which facilitates expanding and makes smooth expanding. There is no particular restriction on the thickness of each portion but it is preferred that the thickness of the substantially non-stretchable portion is from about 40 to 300 μm and the thickness of the expandable portion is from about 30 to 280 μm in the point that the fixing tape can be long wound in a roll form.

Figure 3:
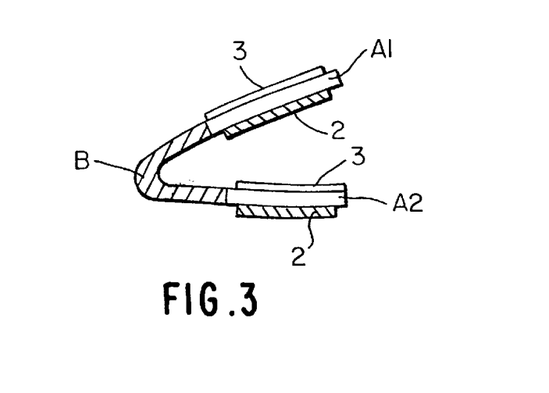
FIG. 3 is a cross sectional view showing another embodiment of the fixing tape of the present invention.

FIG. 3 is a cross sectional view showing another embodiment of the expandable fixing tape of the present invention, wherein a base material, in which both the end portions are substantially non-stretchable portions A1 and A2 and the central portion thereof is an expandable portion B, is folded once at the expandable portion B to constitute a V-form. On the inside surface of the non-stretchable portion A1 and on the outside surface of the non-stretchable portion A2 is formed each of pressure-sensitive adhesive layers 2, and on the outside surface of the non-stretchable portion A1 and on the inside surface of the non-stretchable portion A2 is formed each of releasing agent layers 3.

Figure 4:
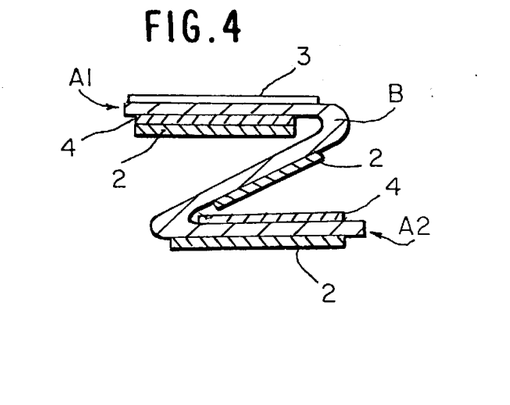
FIG. 4 is a cross sectional view showing still another embodiment of the fixing tape of the present invention.

FIG. 4 is a cross sectional view showing still another embodiment of the expandable fixing tape of the present invention.

In the embodiment shown in FIG. 4, a base material, in which each of both the end portions of the expandable base material is laminated with each of substantially non-stretchable materials (films, etc.) to form each of non-stretchable portions A1 and A2 and the central portion thereof is an expandable portion B, is folded two times to constitute a Z-form. Also, on the inside surface (the non-stretchable material 4 side) of the non-stretchable portion A1 and on the outside surface of the non-stretchable portion A2 is formed each of pressure-sensitive adhesive layers 2 for fixing, on the lower surface of the expandable portion B is formed a pressure-sensitive adhesive layer 2 for temporarily joining is formed, and also on the outside surface of the non-stretchable portion A1 is formed a releasing agent layer 3.

Figure 5:
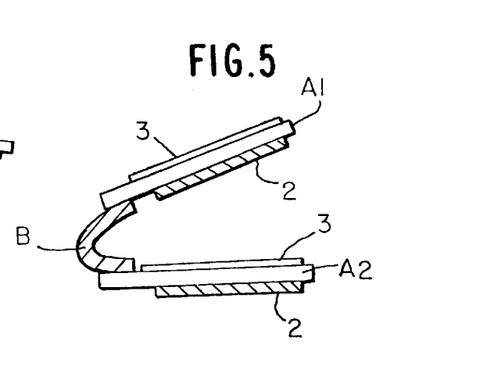
FIG. 5 is a cross sectional view showing still another embodiment of the fixing tape of the present invention.

FIG. 5 is a cross sectional view showing still another embodiment of the expandable fixing tape of the present invention.

In FIG. 5, substantially non-stretchable portions A1 and A2 are separately formed, they are bonded to an expandable portion B by, for example, a heat seal or an adhesive to constitute a base material, and the expandable portion B is folded once to constitute a V-form. On the inside surface of the non-stretchable portion A1 and on the outside surface of the non-stretchable portion A2 is formed each of pressure-sensitive adhesive layers 2 and also on the outside surface of the non-stretchable portion A1 and on the inside surface of the non-stretchable portion A2 is formed each of releasing agent layers 3.

Figure 6:
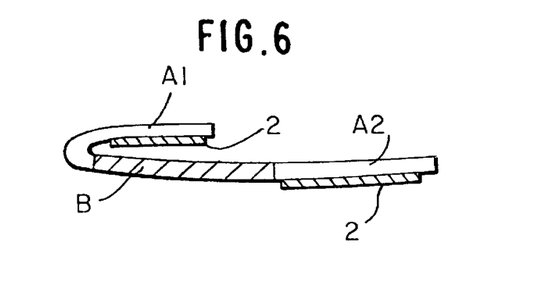
FIG. 6 is a cross sectional view showing still another embodiment of the fixing tape of the present invention.

In FIG. 6, a base material, in which both the end portions are substantially non-stretchable portions A1 and A2 and the central portion thereof is an expandable portion B, is folded once at the non-stretchable portion A1 to constitute a V-form. On the inside surface of the non-stretchable portion A1 and the outside surface of the non-stretchable portion A2 is formed each of pressure-sensitive adhesive layers 2.

Figure 7:
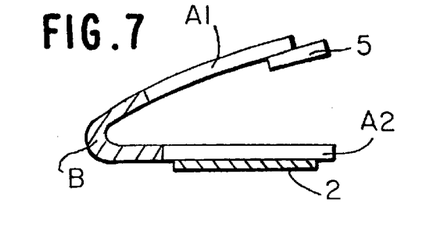
FIG. 7 is a cross sectional view showing still another embodiment of the fixing tape of the present invention.

In FIG. 7, a base material, in which both the end portions thereof are substantially non-stretchable portions A1 and A2 and the central portion thereof is an expandable portion B, is folded once at the expandable portion B to constitute a V-form. On the outside surface of the non-stretchable portion A2 is formed a pressure-sensitive adhesive layer 2 and a pinching piece 5 for improving the facilitate of pinching the fixing tape is formed at the tip portion of the non-stretchable portion A1.

Figure 8:
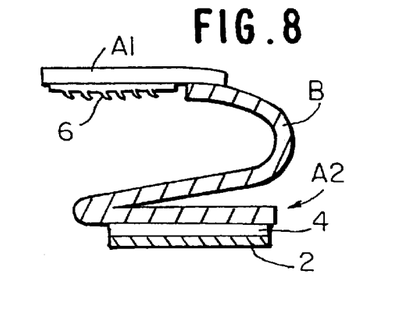
FIG. 8 is a cross sectional view showing still another embodiment of the fixing tape of the present invention.

In FIG. 8, a substantially non-stretchable portion A1 is bonded to an expandable portion B by, for example, a heat seal or an adhesive, a non-stretchable material 4 is laminated on one end portion of the expandable portion B to form a non-stretchable A2, whereby a base material is constituted, and the expandable portion B is folded two times to constitute a Z-form. On the outside surface (the non-stretchable material side 4) of the non-stretchable portion A2 is formed a pressure-sensitive adhesive layer 2. Also, on the inside surface of the non-stretchable portion A1 is formed a fixing means composed of a fastening hook.

Figure 9:
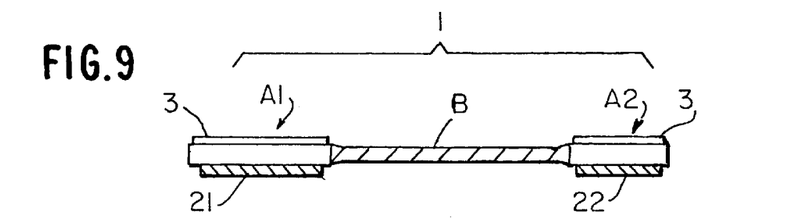
FIG. 9 is a cross sectional view showing still another embodiment of the fixing tape of the present invention.

FIG. 9 shows a fixing tape wherein a base material 1, in which both the end portions thereof are substantially non-stretchable portions A1 and A2 and the central portion thereof is an expandable portion B, is no folded, and on the non-stretchable portion A1 is formed a re-peelable pressure-sensitive adhesive layer 21 for temporarily joining to an article. The fixing tape can be temporarily stuck before use by the re-peelable pressure-sensitive adhesive layer 21 and at use, the tape is released and can be re-adhered. Also, a pressure-sensitive adhesive layer 22 for previously fixing to an article is formed on the non-stretchable portion A2.

Figure 10:
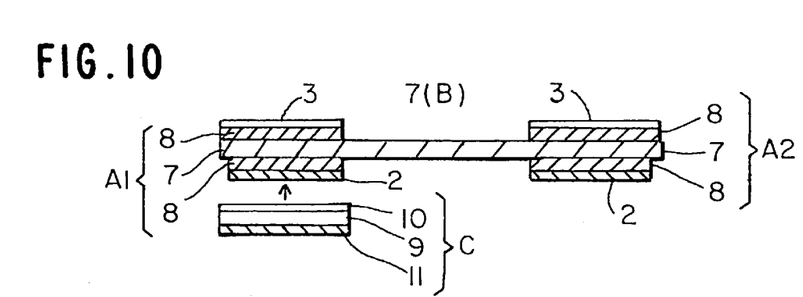
FIG. 10 is a cross sectional view showing still another embodiment of the fixing tape of the present invention.
Figure 11:
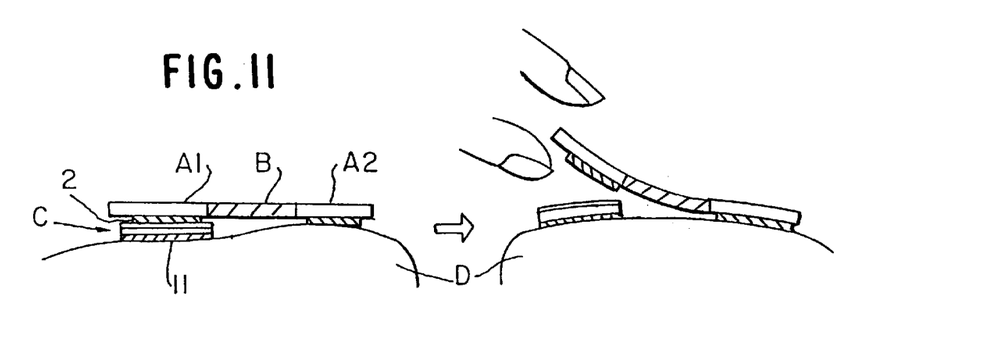
FIG. 11 is a schematic view showing a mode of using the fixing tape of the present invention.

In FIG. 10, a base material is composed of an expandable portion B formed by a stretch film 7 as the central portion and substantially non-stretchable portions A1 and A2 composed of a composite of the stretch film 7 and non-stretchable films 8 at both the end portions thereof, on one surface of each of the non-stretchable portions A1 and A2 is formed each of pressure-sensitive adhesive layers 2 and on each of the other surfaces is formed each of releasing agent layers 3. Furthermore, on the pressure-sensitive adhesive layer 2 of the non-stretchable portion A1 is formed a release tape C composed of a base material 9 having formed on one surface thereof a releasing agent layer 10 and on the other surface a pressure-sensitive adhesive layer 11 such that the pressure-sensitive adhesive layer 2 of the fixing tape of the present invention is in contact with the releasing agent layer 10 of the release tape C. As shown in FIG. 11, such a release tape C is for protecting the surface of the pressure-sensitive adhesive layer 2 of the non-stretchable portion A1 until the use of the fixing tape, and the release tape C can be fixed to an article D via the pressure-sensitive adhesive layer 11 together with the fixing tape of the present invention.

Figure 12:
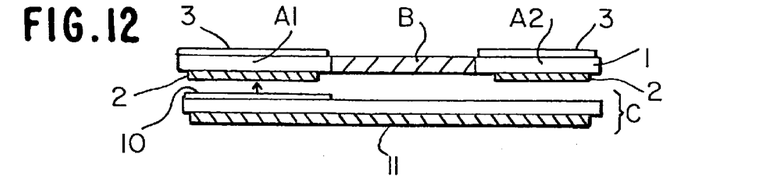
FIG. 12 is a cross sectional view showing still another embodiment of the fixing tape of the present invention.

In FIG. 12, a release tape C as in the release tape C in FIG. 10 has almost the same length as a base material 1 so that the pressure-sensitive adhesive layer 2 of the non-stretchable portion A2 can be protected. On the portion of the release tape C, which is brought into contact with the pressure-sensitive adhesive layer 2 of the non-stretchable portion A1 is formed a releasing agent layer 10 such that the pressure-sensitive adhesive layer 2 can be re-peeled, while no releasing agent is formed on the portion which is brought into contact with the pressure-sensitive adhesive layer 2 of the non-stretchable portion A2 to contact and fix the portion to the pressure-sensitive adhesive layer 2.

By employing the construction, there is an effect that the step gap in the case of winding the fixing tape of this invention together with the release tape C in a roll form can be absorbed.

Figures 13, 14:
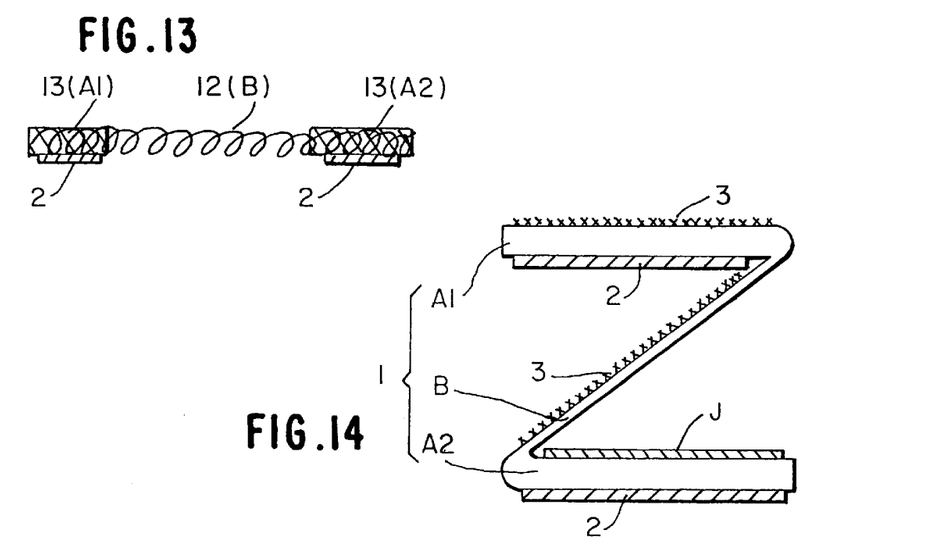
FIG. 13 is a cross sectional view showing still another embodiment of the fixing tape of the present invention.
FIG. 14 is a cross sectional view showing still another embodiment of the fixing tape of the present invention.

FIG. 13 is a cross sectional view showing still another embodiment of the expandable fixing tape of the present invention, wherein both the end portions of a urethane-made nonwoven fabric 12 as an expandable portion B are impregnated with a non-stretchable material 13 such as, for example, an ethylene-vinyl acetate copolymer to form substantially non-stretchable portions A1 and A2 as both the end portions, and each of pressure-sensitive adhesive layer 2 is formed at the non-stretchable portions A1 and A2.

FIG. 14 is a cross sectional view showing still another embodiment of the expandable fixing tape of the present invention, wherein a base material 1 composed of substantially non-stretchable portions A1 and A2, which are thick layer portions, at both the end portions in the lengthwise direction and an expandable portion B, which is a thin layer portion at the central portion between the non-stretchable portions, is folded two times near the boundary between the expandable portion B and the non-stretchable portion A1 and near the boundary between the expandable portion B and the non-stretchable portion A2 to constitute a Z-form. On the inside surface of the non-stretchable portion A1 and on the outside surface of the non-stretchable portion A2 is formed each of pressure-sensitive adhesive layers 2 as fixing means, and on the outside surface of the non-stretchable portion A1 and on the surface of the expandable portion B facing the pressure-sensitive adhesive layer 2 formed at the inside surface of the non-stretchable portion A1 is formed each of releasing agent layers 3. Furthermore, a temporary joining means J (described below) for temporarily joining the expandable portion B to the inside surface of the non-stretchable portion A2 for maintaining the Z-form is formed on the inside surface of the non-stretchable portion A2.

In FIG. 14, the fixing means formed on the outside surface of the non-stretchable portion A2 is necessary for fixing one end of the fixing tape to an adherend and the pressure-sensitive adhesive layer 2 as shown in FIG. 14 is preferably used, but such a fixing means is no limited to a pressure-sensitive adhesive layer and according to the kind of the adherend, other fixing means such as, for example, an adhesive or a hook-form fastening object can be employed.

Also, in FIG. 14, the embodiment of having the fixing means for re-peeling, which is composed of the pressure-sensitive adhesive layer 2 on the inside surface of the non-stretchable portion A1, is illustrated. But, not only the pressure-sensitive adhesive layer 2 but also other means such as an adhesive or a hook-form fadepending on the fore employed depending on the form or kind of an adherend.

Figure 15:
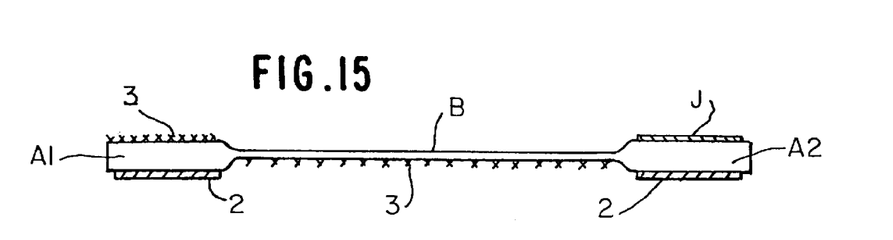
FIG. 15 is a schematic view at unfolding the fixing tape of FIG. 14.

FIG. 15 is a schematic view showing the state of unfolding the fixing tape of FIG. 14 at use. For example, by pulling the non-stretchable portion A1, the temporary joining means J is released to unfold the Z-form and by further pulling the non-stretchable portion A1, the expandable portion B is expanded to a necessary length and can be fixed to an adherend with the pressure-sensitive adhesive layer 2.

The expandable portion B is necessary for prolonging the total length of the fixing tape to surround an article with the tape and to fix the tape onto the article. It is preferred that the expandable portion B is expanded by a weak force at use for the purpose of reducing a stress, which is caused by pulling with a hand, by expanding of the tape, preventing one end of the fixing tape previously fixed to an article from being released, and reducing a stress caused by a little expansion of the article after rounding the article. Specifically, it is preferred that the fixing tape can be expanded to the length of at least three times under a load of 1.5 kg/25 mm and at 23° C. If the expandable property of the expandable portion B is less than three times, there is a fault that a large force becomes required for expanding the tape to a definite length, whereby one end of the fixing tape previously fixed is released, the fixing tape is reluctant to expand and is reluctant to use.

Furthermore, for the purpose of treating (wasting) an article having the various circumferences by surrounding it with the fixing tape, freely controlling the total length of the fixing tape with a hand, or restraining expansion of the article after the fixing tape was fixed onto the article, it is preferred that the expandable portion B is not shrinked too much after being expanded and the expandable portion B does not shrink to the original length after releasing the force. Specifically, it is desirable that the permanent set (at 23° C.) at 200% expanding of the expandable portion B is at least 30%, and particularly at least 50%. After expanding, if the expandable portion B largely shrinks to the original state, the shrinking force is large, whereby there occurs a fault that the end portion of the fixing tape previously fixed to an article or the portion of fixing an article after rounding is released. However, the occurring of a little shrinkage is rather preferable in the point of capable of rounding an article in a strained state.

Also, since a fixing means such as a pressure-sensitive adhesive layer, an adhesive layer, a fastening object (hook-form object), etc., is formed on the substantially non-stretchable portions A1 and/or A2 for fixing an article thereto, if the expansion thereof is large, there is a possibility that the fixed portion is released by expanding, it is preferred that the non-stretchable portion is substantially reluctant to expand and it is desirable that the non-stretchable portions have the ductility only of less than 2 times and particularly less than 1.5 times under the load of 1 kg/25 mm. However, the occurrence of a little expansion is preferred in the point that the concentration of stresses in the bonded portion of the expandable portion and the non-stretchable portion is absorbed by the little expansion of the non-stretchable portion, whereby the strength can be retained.

Also, in the present invention, as shown in FIG. 15, for easily and smoothly expanding the expandable portion B and also prolong the total length of the fixing tape by the expansion of the expandable portion B and surround an article with the tape and fixing, it is preferred that the thickness of the expandable portion B, which is the central portion in the lengthwise direction of the base material is thinner than the thickness of the non-stretchable portions A1 and A2 at both the end portions. Specifically, it is preferred that the thickness of the expandable portion B, which is the thin layer portion, is not more than 90%, and more preferably not more than 70% of the thickness of the substantially non-stretchable portions A1 and A2, which are thick portions.

If the thickness of the expandable portion B is over 90% of the thickness of the non-stretchable portions A1 and A2, at expanding the fixing tape to a desired length, not only the expandable portion B but also the non-stretchable portions A1 and A2 are expanded, whereby the tape becomes reluctant to fix an article and the fixed portion is released.

There is no particular restriction on the thickness of each portion if the thickness satisfies the foregoing condition but it is preferred that the thickness of the non-stretchable portion is from about 40 to 300 μm and the thickness of the expandable portion is from about 30 to 280 μm from the point that the fixing tape can be long wound in a roll form.

Figure 16:
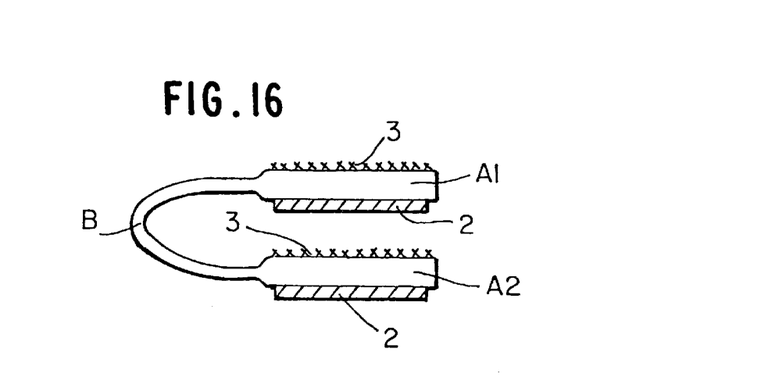
FIG. 16 is a cross sectional view showing still another embodiment of the fixing tape of the present invention.

FIG. 16 is a cross sectional view showing still another embodiment of the expandable fixing tape of the present invention, wherein a base material composed of substantially non-stretchable portions A1 and A2 having a thick thickness at both the end portions and an expandable portion B having a thin thickness at the central portion between the non-stretchable portions is folded once at the expandable portion B to constitute a U-form. On the inside surface of the non-stretchable portion A1 and the outside surface of the non-stretchable portion A2 is formed each of pressure-sensitive adhesive layers 2 and on the outside surface of the non-stretchable portion A1 and on the inside surface of the non-stretchable portion A2 is formed each of releasing agent layers 3.

Figure 17:
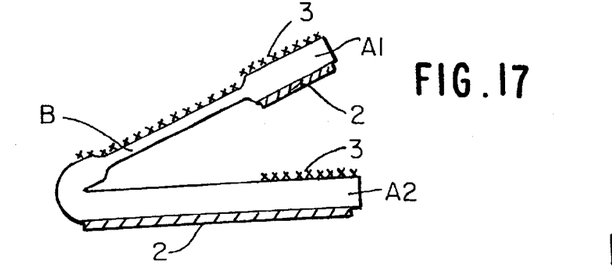
FIG. 17 is a cross sectional view showing still another embodiment of the fixing tape of the present invention.

FIG. 17 is a cross sectional view showing still another embodiment of the expandable fixing tape of the present invention, wherein a base material composed of substantially non-stretchable portions A1 and A2 having a thick thickness at both the end portions and an expandable portion B having a thin thickness at the central portion between the non-stretchable portions is folded at the end portion of the non-stretchable portion A2 to constitute a V-form. On the inside surface of the non-stretchable portion A1 and the outside surface of the non-stretchable portion A2 is formed each of pressure-sensitive adhesive layers 2 and on the outside surface of the non-stretchable portion A1, on the outside surface of the expandable portion B, and on a part (the surface facing the pressure-sensitive adhesive layer 2 formed at the inside surface of the non-stretchable portion A1) of the inside surface of the non-stretchable portion A2 is formed each of releasing agent layers 3.

Figure 18:
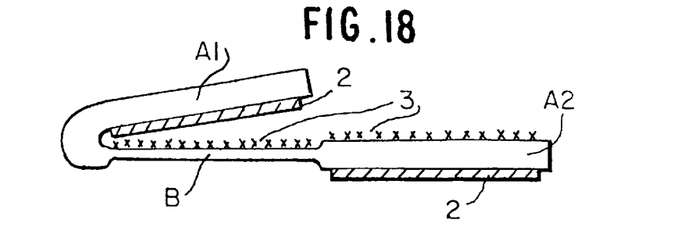
FIG. 18 is a cross sectional view showing still another embodiment of the fixing tape of the present invention.

FIG. 18 is a cross sectional view showing still another embodiment of the expandable fixing tape of the present invention, wherein a base material composed of substantially non-stretchable portions A1 and A2 having a thick thickness at both the end portions and an expandable portion B having a thin thickness at the central portion between the non-stretchable portions is folded at the end portion of the non-stretchable portion A1 to constitute a V-form. On the inside surface of the non-stretchable portion A1 and on the outside surface of the non-stretchable portion A2 is formed each of pressure-sensitive adhesive layers 2 and on the inside surface of the expandable portion B and on the inside surface of the non-stretchable portion A2 is formed each of releasing agent layers 3.

Figure 19:
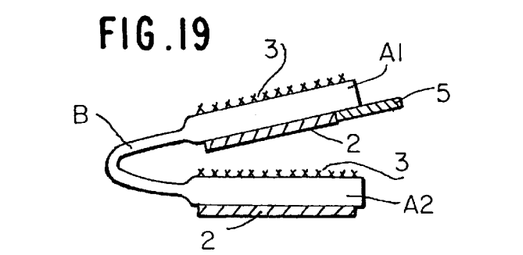
FIG. 19 is a cross sectional view showing still another embodiment of the fixing tape of the present invention.

FIG. 19 is a cross sectional view showing still another embodiment of the expandable fixing tape of the present inventing, wherein a base material composed of substantially non-stretchable portions A1 and A2 having a thick thickness at both the end portions and an expandable portion B having a thin thickness at the central portion between the non-stretchable portions is folded once at the expandable portion B to constitute a V-form. On the inside surface of the non-stretchable portion A1 and on the outside surface of the non-stretchable portion A2 is formed each of pressure-sensitive adhesive layers 2, on the outside surface of the non-stretchable portion A1 and on the inside surface of the non-stretchable portion A2 is formed each of releasing agent layers 3, and further a pinching piece 5 for improving pinching property of the fixing tape is formed at the tip of the inside surface of the non-stretchable portion A1.

Figure 20:
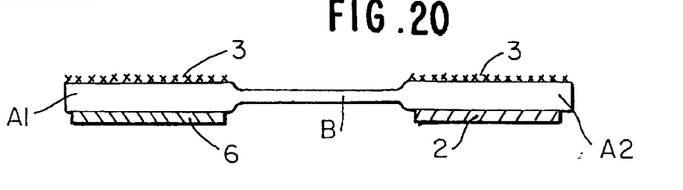
FIG. 20 is a cross sectional view showing still another embodiment of the fixing tape of the present invention.

FIG. 20 is a cross sectional view showing still another embodiment of the expandable fixing tape of the present invention and the tape is composed of a base material wherein both the end portions in the lengthwise direction are substantially non-stretchable portions A1 and A2 having a thick thickness and the central portion between the non-stretchable portions is an expandable portion B having a thin thickness. On one surface of the non-stretchable portion A2 is formed a pressure-sensitive adhesive layer 2 for fixing to an article and on one surface of the non-stretchable portion A1 is formed a re-peelable pressure-sensitive adhesive layer 6 for temporarily joining the tape to an article. On the other surfaces of the non-stretchable portions A1 and A2, each releasing agent layer 3 is provided. By the existence of the re-peelable pressure-sensitive adhesive layer 6, the fixing tape can be temporarily stuck to an article before use and at use, the tape is released from the article and can be re-adhered.

Figure 21:
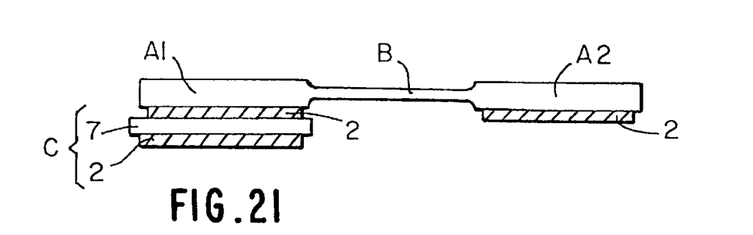
FIG. 21 is a cross sectional view showing still another embodiment of the fixing tape of the present invention.

FIG. 21 is a cross sectional view showing still another embodiment of the expandable fixing tape of the present invention and the tape is composed of a base material, wherein both the end portions thereof are substantially non-stretchable portions A1 and A2 having a thick thickness and the central portion between the non-stretchable portions is an expandable portion B having a thin thickness, and on one surface of each of the non-stretchable portions A1 and A2 is formed a pressure-sensitive adhesive layer 2. Furthermore, on the pressure-sensitive adhesive layer 2 of the non-stretchable portion A1 is formed a release tape C composed of a base material 7 having formed one surface thereof a pressure-sensitive adhesive layer 2 such that the pressure-sensitive adhesive layer 2 formed at the non-stretchable portion A1 of the fixing tape of this invention is in contact with the base material 7 of the release tape C. The release tape C is for protecting the surface of the pressure-sensitive adhesive layer 2 before using the fixing tape, and the release tape C can be fixed to an article together with the fixing tape of this invention via the pressure-sensitive adhesive layer 2.

Figure 22:
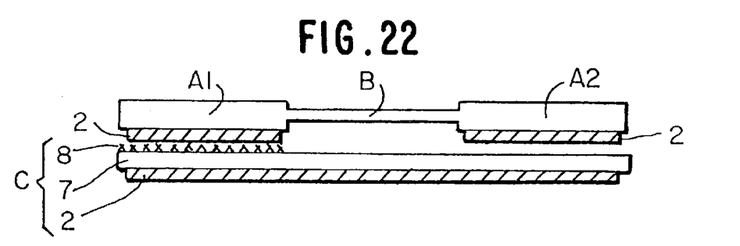
FIG. 22 is a cross sectional view showing still another embodiment of the fixing tape of the present invention.

In the embodiment shown by FIG. 22, the release tape C as shown in FIG. 21 has almost the same length as the base material so that the release tape C can also protect the pressure-sensitive adhesive layer 2 formed at the non-stretchable portion A2 together with the pressure-sensitive adhesive layer 2 formed at the non-stretchable portion A1. Also, on the portion of the base material 7 of the release tape C, which is brought into contact with the pressure-sensitive adhesive layer 2 formed at the non-stretchable portion A1, is formed a releasing agent layer 8 such that the release tape can be re-released, and on the portion of the base material 7, which is brought into contact with the pressure-sensitive adhesive layer 2 formed at the non-stretchable portion A2, is not formed a releasing agent layer. The portion of the release tape C is adhered and fixed to the fixing tape of the present invention. By employing the foregoing construction, there is an effect of absorbing the step gap formed in the case of winding the fixing tape of the present invention together with the release tape C in a roll form.

In the present invention, by temporarily joining the lower surface of the expandable portion B of the fixing tape folded in a Z-form as shown in FIG. 1 and FIG. 14 to the inside surface of the non-stretchable portion A2 facing the foregoing lower surface, it is possible that the Z-form is not opened before using the fixing tape. There is no particular restriction on the temporary joining means J, but they can be temporarily stuck to each other by, e.g., a heat seal, a hot melt series, melt blow type, or fibrous pressure-sensitive adhesive or adhesive, and an embossing system by press.

There is no particular restriction on each part of the expandable fixing tape of the present invention as long as the tape has the characteristics described above.

As the base material, polyolefin series plastic films such as polypropylene, polyethylene, ethylenepropylene rubber, or a mixture thereof, etc.; and elastomer films such as polystyrene series films, polyester series films, urethane series films, etc., can be preferably used singly or as a mixture thereof. The base material composed of the non-stretchable portion and the expandable portion can be prepared by an extrusion molding method by a T die, an inflation, etc., although the method is not limited to these methods.

As the substantially non-stretchable portion, a polyolefin type plastic film is preferably used, and examples thereof include polypropylene and a blend of polypropylene and polyethylene. Furthermore, the expandable portion described below can be converted into a substantially non-stretchable portion by laminating the expandable portion with a non-stretchable material such as polypropylene, polyethylene terephthalate, an ethylene-vinyl acetate copolymer, and a paper onto the expandable portion (FIG. 4) or by impregnating the expandable portion with the foregoing non-stretchable material (FIG. 13).

Also, as the expandable portion, a material substantially not showing stretch back (shrinkage after expanding) is preferred and a material becoming a string for by necking may be used. As the material, in particular, polyolefin series plastic films such as random polypropylene, low-density polyethylene, linear low-density polyethylene (L-LDPE), etc., are preferably used singly or as a blend thereof. Furthermore, styrene series, polyester series and urethane series elastomer films, and woven fabrics or nonwoven fabrics made of fibers of these polymers are also preferable.

The base material composed of the substantially non-stretchable portions and the expandable portion can be obtained by a method of forming a composite type material by the impregnation and lamination of the foregoing materials or can be obtained by a co-extrusion method. From the point of the productivity, a co-extrusion type method is particularly preferred.

Figures 23A, 23B:
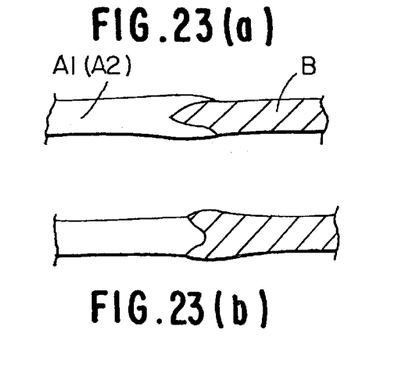
FIG. 23 is a partially enlarged cross sectional view showing the bonded portion of the base material of the fixing tape of the present invention.
Figure 24:
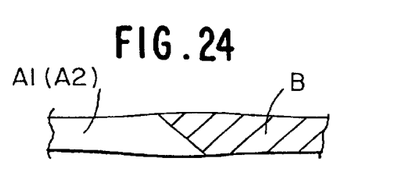
FIG. 24 is a partially enlarged cross sectional view showing another embodiment of the bonded portion of the base material of the fixing tape of the present invention.

In the present invention, when the substantially non-stretchable portions A1 and A2 and the expandable portion B of the base material 1 are, for example, integral molded as shown in FIG. 9 by a profile extrusion method in a width direction, it is preferred that the structure of the bonded portion of them is the structure that the non-stretchable portion A1 or A2 is bonded to the expandable portion B each other in a wedge form as shown in FIG. 23 or the structure that at least one portion is overlapped the other portion as shown in FIG. 24 from the point of the strength. By employing such a structure, the contact area of the interface between the non-stretchable portion A1 or A2 and the expandable portion B can be increased, which gives the effect that the concentration of stress can be reduced. Furthermore, the structure of FIG. 23 is a particularly preferred structure in a construction of a fracture mode in which after expanding the expandable portion B, the overlapped portion is expanded a little, and then, the non-stretchable portion A1 or A2 is expanded.

Also, there is no particular restriction on the material for the pressure-sensitive adhesive layer, there are, for example, a rubber series material and an acrylic material. Furthermore, there is no particular restriction on the material for the releasing agent layer, there are a silicone series material, a non-silicone series material (long chain alkyl series materials, etc.), etc.

Figure 26:
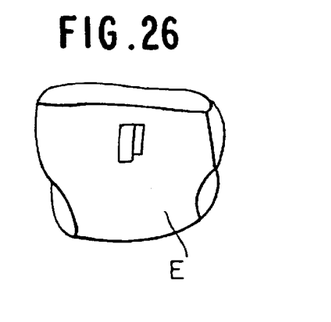
FIG. 26 is a schematic view showing a mode of using the fixing tape of the present invention.
Figure 27:
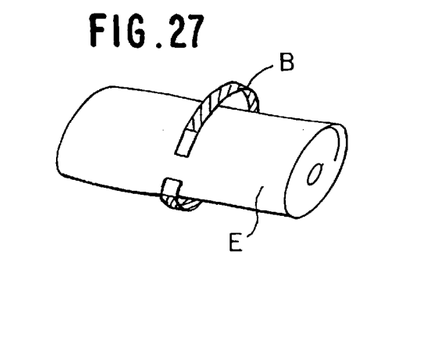
FIG. 27 is a schematic view showing another embodiment of a mode of using the fixing tape of the present invention.

In the case of using the expandable fixing tape of the present invention, the non-stretchable portion A2 is fixed on the surface of, for example, a diaper E with the pressure-sensitive adhesive layer 2 as shown in FIG. 26 and in the case of treating rounding the diaper after using the diaper as shown in FIG. 27, the non-stretchable portion A1 is pulled out, the expandable portion B is expanded as shown in FIG. 2 and the fixing tape can be fixed to the rounded diaper E.

Figure 28:
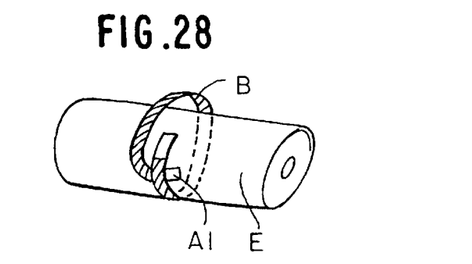
FIG. 28 is a schematic view showing still another embodiment of a mode of using the fixing tape of the present invention.

Also, the expandable fixing tape of the present invention can be used as the type where the non-stretchable portion A1 is not pressure-sensitive and does not have a fixing means, that is, after winding the expandable portion B around an article, the fixing tape can be fixed by putting in the non-stretchable portion A1 as shown in FIG. 28.

Figure 29:
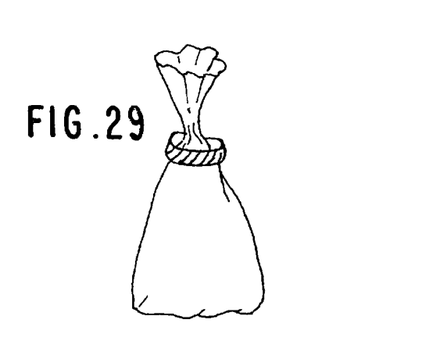
FIG. 29 is a schematic view showing still another embodiment of a mode of using the fixing tape of the present invention.
Figure 30:
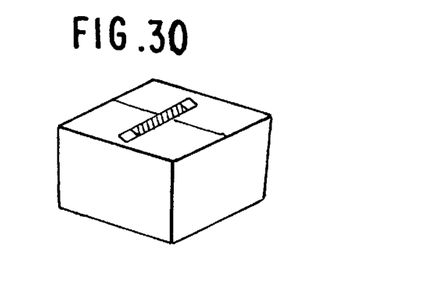
FIG. 30 is a schematic view showing still another embodiment of a mode of using the fixing tape of the present invention.

Also, the expandable fixing tape of the present invention can be used for a package of a bag (FIG. 29) or for a package of a box (FIG. 30).

Then, the present invention is described practically by the following examples.

EXAMPLE 1-1

As a central portion, linear low-density polyethylene was used, as both end portions, a blend of polyethylene and polypropylene (30/70 by weight) was used, and a base material film (160 mm width) composed of the central portion (=expandable portion) (60 mm width, 50 $\mu$m thickness) and both end portions (=substantially non-stretchable portions) (50 mm width, 60 $\mu$m thickness) was obtained by a co-extrusion method at a temperature of from 160 to 200°C.

On both the end portions (=substantially non-stretchable portions) of the base material film was coated a rubber series pressure-sensitive adhesive at a thickness of 40 $\mu$m, on the base material portion in contact with the pressure-sensitive adhesive was coated a releasing agent, and the base material film was folded in a Z-form as shown in FIG. 1 to provide a sample of the fixing tape of the present invention.

EXAMPLE 1-2

Linear low-density polyethylene was extruded at a temperature of from 160 to 200° C. to obtain a film having a width of 160 mm and a thickness of 100 $\mu$m. Then, on both the end portions of the film was provided each of polyester films having a width of 50 mm and a thickness of 38 $\mu$m with a pressure-sensitive adhesive as substantially non-stretchable portions to provide a base material film. On the substantially non-stretchable portions was formed each of acrylic pressure-sensitive adhesive layers having a thickness of 40 $\mu$m and the base material film was folded in a Z-form as shown in FIG. 4 to provide a sample of the fixing tape of the present invention.

EXAMPLE 1-3

Both the end portions of a urethane-made nonwoven fabric (160 mm width, basis weight 80 g/m$^2$) were impregnated with an ethylene-vinyl acetate copolymer (50 mm width) to form substantially non-stretchable portions. On the non-stretchable portions was coated each of rubber series pressure-sensitive adhesive at a thickness of 40 $\mu$m to provide a sample of the fixing tape of the present invention as shown in FIG. 13.

comparative example 1-1

A fixing tape was prepared in the same manner as Example 1-1 except that the total thickness of the base material film was changed to 300 $\mu$m.

comparative example 1-2

A fixing tape was prepared in the same manner as Example 1-2 except that the central portion and both the end portions were all composed of linear low-density polyethylene (20 $\mu$m thick).

comparative example 1-3

Both the end portions of a nylon-made nonwoven fabric (160 mm width, basis weight 80 g/m$^2$) were coated with a rubber series pressure-sensitive adhesive having a thickness of 40 $\mu$m to provide a fixing tape.

The properties of each portion of the fixing tape samples obtained in the examples and the comparative examples were measured according to the following methods under the conditions shown in Table 1 below. The results are shown in Table 1.

Expandable Property of Expandable Portion

Each sample was expanded by Tensilon (universal tester) at a tensile speed of 300 mm/minute under an atmosphere of 23° C., and the load (kg/25 mm) at when the expandable portion had the length three times the initial length of the expandable portion (i.e., at 200% expanding) was measured.

Ductility of Non-stretchable Portion

The non-stretchable portion of each sample was cut into 25 mm width, a load of 0.5 kg was hung in the perpendicular direction under the atmosphere of 23° C., and the length at that time was measured. The ductility was obtained as $L_2/L_1$ (times).

$L_1$: Initial length; $L_2$: Length after expanding

Permanent Set

Each sample (initial length: $a_1$) was subjected to 200% expanding by Tensilon at a tensile speed of 300 mm/minute under the atmosphere of 23° C. After allowing to stand for 3 minutes, the force was released and the length of the sample (length: $a_2$) was measured. The permanent set was calculated by the following formula.

$$(a_2-a_1)/a_1 \times 100(\%)$$

$a_1$: Initial length $a_2$: Length measured after the force to expand the sample was released

TABLE 1

|  | Expandable Portion | | Non-stretchable Portion Ductility[3] (times) |
|---|---|---|---|
|  | Load[1] (kg/25 mm) | Permanent Set[2] (%) |  |
| Example 1-1 | 1.8 | 60 | 1.22 |
| Example 1-2 | 3.7 | 70 | 1.12 |
| Example 1-3 | 0.8 | 38 | 1.75 |
| Comparative Example 1-1 | 5.4 | 82 | 1.02 |
| Comparative Example 1-2 | 0.8 | 60 | 4.54 |
| Comparative Example 1-3 | ruptured | ruptured | 1.11 |

Note)
[1] at 200% expanding
[2] at 200% expanding
[3] under the load of 0.5 kg/25 mm Monitor Test Each of the samples of the fixing tapes obtained in the examples and the comparative examples was practically used by 20 men and 20 women by the using method of rounding a paper diaper of an underpants type (as shown in FIG. 26) and was evaluated in the terms of practical use. The results are shown in Table 2 below.

TABLE 2

|  | Usability | Fixability | Roundability | Others | Total Evaluation |
|---|---|---|---|---|---|
| Example 1-1 | A | A | A | easily usable | A |
| Example 1-2 | A | A | A | easily usable | A |
| Example 1-3 | A | A | A | soft | A |
| Comparative Example 1-1 | C | B | C | (a) | C |
| Comparative Example 1-2 | C | C | C | (b) | C |
| Comparative Example 1-3 | C | C | C | (c) | C |

Evaluation in the above table:
A: Not less than 30 persons in 40 persons answered "good".
B: From 10 to 29 persons in 40 persons answered "good".
C: Less than 10 persons in 40 persons answered "good".
(a): It was not so easy to use because of being solid.
(b): It was too soft to be used easily.
(c): It was not so easy to use because it did not expand but cut.

Breaking Strength Test of Base Material

Figure 25:
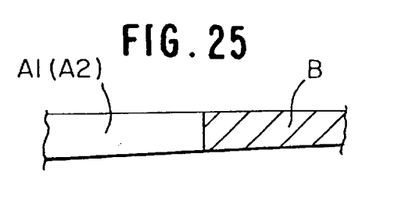
FIG. 25 is a partially enlarged cross sectional view showing still another embodiment of the bonded portion of the base material of the fixing tape of the present invention.

Samples (width 25 mm), in which each of the structure of the bonded portion of the expandable portion and the non-stretchable portion of the base material used in Example 1-1 was changed as shown in from FIG. 23 to FIG. 25, were prepared. Each sample was subjected to a breaking test by Tensilon at a tensile speed of 300 mm/minutes and a distance between chucks of 100 mm. The obtained results are shown in Table 3.

TABLE 3

|  | FIG. 23 (a) | FIG. 23 (b) | FIG. 24 | FIG. 25 |
|---|---|---|---|---|
| Overlapped Portion | Both sides 2.0 mm | Both sides 1.0 mm | One side 0.5 mm | none |
| Breaking Strength (kg/25 mm) | 3.8 | 3.0 | 2.8 | 1.5 |
| Breaking Mode | (P) | (Q) | (Q) | (R) |

(P): After the non-stretchable portion expanded a little, the sample was broken.
(Q): After the bonded portion expanded, the sample was broken.
(R): The sample was cut at the bonded portion.

From the results, it can be seen that when the overlapped portion of the bonded portion of the expandable portion and the non-stretchable portion is at least 0.5 mm, the bonded portion has a sufficient breaking strength. The length of the overlapped portion means the length of the overlapped portion in the lengthwise direction of the tape.

In the following examples, the base materials were all produced by a T-die extrusion method. The melt flow rate (MFR) of polypropylene and polyethylene were measured at 230° C. and 190° C., respectively, according to ASTM-D-1238.

EXAMPLE 2-1

Using a blend of polypropylene (density 0.89 g/cm$^3$, MFR 6.0 g/10 minutes)/polyethylene (density 0.92 g/cm$^3$, MFR 9.0 g/10 minutes)=80/20 by weight, a base material of 50 mm width composed of non-stretchable portions (thick layer portions) having a thickness of 120 μm and a width of 50 mm and an expandable portion (thin layer portion) having a thickness of 60 μm (50% of the thickness of the non-stretchable portions) and a width of 50 mm was obtained.

Both the end portions (non-stretchable portions) of the base material were coated with a rubber series pressure-sensitive adhesive at a thickness of 40 μm, the base material portion in contact with the pressure-sensitive adhesive was coated with a releasing agent, and the base material was folded in a Z-form as shown in FIG. 14 to provide a sample of the fixing tape of the present invention.

EXAMPLE 2-2

Using a blend of polypropylene (density 0.89 g/cm$^3$, MFR 6.0 g/10 minutes)/linear low-density polyethylene (density 0.93 g/cm³, MFR 2.1 g/10 minutes, Ultzex 2520F, trade name, made by Mitsui Petrochemical Industries, Ltd.)=60/40 by weight, a base material composed of non-stretchable portions (thick layer portions) having a thickness of 140 μm and a width of 50 mm and an expandable portion (thin layer portion) having a thickness of 70 μm (50% of the thickness of the non-stretchable portions) and a width of 50 mm was obtained. Thereafter, by following the same procedure as in Example 2-1 except for using the base material, a fixing tape of the present invention was obtained.

comparative example 2-1

Using polypropylene (density 0.89 g/cm³, MFR 6.0 g/10 minutes), a base material composed of non-stretchable portions (thick layer portions) having a thickness of 300 μm and a width of 50 mm and an expandable portion (thin layer portion) having a thickness of 150 μm (50% of the non-stretchable portions) and a width of 50 mm was obtained. Thereafter, by following the same procedure as in Example 2-1 except for using the base material, a sample of a fixing tape was obtained.

comparative example 2-2

Using SEBS (styrene-ethylene-butylene-styrene) having a density of 0.89 g/cm³ and a MFR of 9.5 g/10 minutes (Tuftec H1052 made by Asahi Chemical Industry Co., Ltd.), a base material composed of non-stretchable porions (thick layer portions) having a thickness of 150 μm and a width of 50 mm and an expandable portion (thin layer portion) having a thickness of 70 μm (47% of the thickness of the non-stretchable portions) and a width of 50 mm was obtained. Thereafter, by following the same procedure as in Example 2-1 except for using the base material, a sample of a fixing tape was obtained.

comparative example 2-3

Using linear low-density polyethylene (density 0.92 g/cm², MFR 1.0 g/10 minutes; Afinity EG8100, trade name, made by Dow Chemical Japan Co.), a base material composed of non-stretchable portions (thick layer portions) having a thickness of 100 μm and a width of 50 mm and an expandable portion (thin layer portion) having a thickness of 50 μm (50% of the thickness of the non-stretchable portions) and a width of 50 mm was obtained. Thereafter, by following the same procedure as in Example 2-1 except for using the base material, a sample of a fixing tape was obtained.

comparative example 2-4

Using the same blend for the base material in Example 2-2, a base material composed of non-stretchable portions (thick layer portions) having a thickness of 90 μm and a width of 50 μm and an expandable portion (thin layer portion) having a thickness of 85 μm (94% of the thickness of the non-stretchable portions) and a width of 50 mm was obtained. Thereafter, by following the same procedure as in Example 2-1, a sample of a fixing tape was obtained.

The properties of each portion of the fixing tape samples obtained in Examples 2-1 and 2-2 and Comparative Examples 2-1 to 2-4 were measured by the following methods under the conditions shown in Table 4 below and the results are shown in Table 4.

Ductility

Each sample was cut into a width of 25 mm and a length of 40 mm, a load of each weight was hung in the perpendicular direction under the atmosphere of 23° C., and the length (mm) at that time was measured and designated as $L_1$. The value given by $L_1/40$ (times) was shown in Table 4.

Permanent Set

Each sample (25 mm width, 40 mm length) was subjected to 200% expending by tensilon at a tensile speed of 300 mm/minute under the atmosphere of 23° C., after allowing to stand the system for 3 minutes, the force was released, and after 3 minutes, the length of the sample was measured and designated as $L_2$. The permanent set given by $(L_2-40)/40 \times 100$ (%) was shown in Table 4 below.

TABLE 4

|  | Thin Layer Portion | | Thick Layer Portion |
|---|---|---|---|
|  | Ductility[1] (times) | Permanent Set[2] (%) | Ductility[3] (times) |
| Example 2-1 | 4.5 | 40 | 1.2 |
| Example 2-2 | 5.2 | 60 | 1.4 |
| Comparative Example 2-1 | 1.9 | 75 | 1.0 |
| Comparative Example 2-2 | 5.0 | 10 | 1.4 |
| Comparative Example 2-3 | 8.1 | 65 | 3.6 |
| Comparative Example 2-4 | 4.0 | 60 | 1.5 |

Note)
[1] under the load of 1.5 kg/25 mm
[2] at 200% expanding
[3] under the load of 1 kg/25 mm Monitor Test Each of the fixing tape samples in Examples 2-1 and 2-2 and Comparative Examples 2-1 to 2-4 was fixed to a paper diaper of an underpants type, 20 men and 20 women made a work of rounding the paper diaper of an underpants type, expanding each fixing tape sample and fixing the sample to evaluate the practical usability under the following standards.

A: Not less than 30 persons in the 40 persons answered "good".

B: From 10 to 29 persons in the 40 persons answered "good".

C: Not more than 9 persons in the 40 persons answered "good".

With respect to the evaluation of release of tape, the actual number was noted.

The results obtained are shown in Table 5 below.

TABLE 5

|  | Expandability | Fixability | Roundability | Usability | Release of Tape | Total Evaluation |
|---|---|---|---|---|---|---|
| Ex. 2-1 | A | A | A | (p) | 0/40 | A |
| Ex. 2-2 | A | A | A | (p) | 0/40 | A |
| CE. 2-1 | C | B | C | (q) | 2/40 | C |
| CE. 2-2 | B | C | B | (r) | 19/40 | C |
| CE. 2-3 | A | A | A | (p) | 15/40 | C |
| CE. 2-4 | A | C | B | (s) | 23/40 | C |

Note)
Ex.: Example; CE.: Comparative Example
(p): Easily usable; (q): Solid
(r): Reluctant to use; (s): Reluctant to fix As described above, since the expandable fixing tape of the present invention can be easily expanded by a weak force at use and the expanded portion is reluctant to shrink, the fixing tape has the advantages that articles having various surrounding lengths can be packed with the fixing tape by rounding each article and fixing the tape to the rounded article, and further the length of the fixing tape can be desirably controlled for packaging.

While the invention has been described in detail with reference to specific embodiments, it will be apparent to one skilled in the art that various changes and modifications can be made to the invention without departing from its spirit and scope.

What is claimed is:

1. An expandable fixing tape comprising:

a base material composed of an expandable portion and a substantially non-stretchable portion, and a fixing means provided on at least one non-stretchable portion which is present on at least one end of the base material, wherein the expandable portion exhibits a load (tension) of not more than 5.0 kg/25 mm when it is subjected to 200% expanding and a permanent set of not less than 30% under the condition of 200% expanding, and the substantially non-stretchable portion has a ductility of less than twice under a load of not more than 0.5 kg/25 mm, and wherein both the end portions of the base material are substantially non-stretchable portions, the central portion thereof is the expandable portion, and the thickness of the expandable portion is thinner than the thickness near the boundary of the non-stretchable portion and the expandable portion.

2. The expandable fixing tape of claim 1, wherein a fixing means is formed on the non-stretchable portion(s) at both the end portions or one end portion of the base material.

3. The expandable fixing tape of claim 1, wherein the fixing means is a pressure-sensitive adhesive or a fastening means.

4. The expandable fixing tape of claim 1, wherein the fixing tape is folded at least once.

5. The expandable fixing tape of claim 4, wherein the fixing tape is folded in a Z-form or a V-form.

6. The expandable fixing tape of claim 4, wherein the folded state of the fixing tape is maintained by a temporary joining means.

7. An expandable fixing tape according to claim 1, wherein the thickness of the expandable portion is not more than 90% of the thickness of the non-stretchable portion.

8. An expandable fixing tape according to claim 1, wherein the tape is for treating an article.

9. An expandable fixing tape comprising:

a base material composed of an expandable portion, which is a thin layer portion having a thin thickness, at the central portion in the lengthwise direction and substantially non-stretchable portions, which are thick layer portions having a thick thickness, at both the end portions, a fixing means provided on at least one non-stretchable portion which is present on at least one end of the base material, wherein the expandable portion can be expanded to the length of at least three times under a load of 1.5 kg/25 mm and has a permanent set of at least 30% under the condition of 200% expanding, and the thickness of the expandable portion is not more than 90% of the thickness of the non-stretchable portion.

10. The expandable fixing tape of claim 9, wherein the substantially non-stretchable portions, which are thick layer portions, of the base material have a ductility of less than twice under a load of 1 kg/25 mm.

11. The expandable fixing tape of claim 9, wherein the fixing means is a pressure-sensitive adhesive or a fastening means.

12. The expandable fixing tape of claim 9, wherein the fixing tape is folded at least once.

13. The expandable fixing tape of claim 12, wherein the fixing tape is folded in a Z-form or a V-form.

14. The expandable fixing tape of claim 12, wherein the folded state of the fixing tape is maintained by a temporary joining means.

* * * * *